US00PP10183P

United States Patent [19]

Jacobsen

[11] Patent Number: Plant 10,183

[45] Date of Patent: Jan. 6, 1998

[54] POINSETTIA PLANT 'PEPRIDE'

[75] Inventor: Peter Jacobsen, deceased, late of Skibby, Denmark, by Aase Jacobsen, executrix

[73] Assignee: Paul Ecke Ranch, Inc., Encinitas, Calif.

[21] Appl. No.: 630,432

[22] Filed: Apr. 10, 1996

[51] Int. Cl.[6] ..... A01H 5/00

[52] U.S. Cl. ..... Plt./86.4

[58] Field of Search ..... Plt./86.4

[56] References Cited

PUBLICATIONS

UPOVROM Citation "Pepride" for a Poinsettia by Aase Jacobsen Apr. 15, 1994.

*Primary Examiner*—James R. Feyrer

*Attorney, Agent, or Firm*—Arnold, White & Durkee

[57] ABSTRACT

Poinsettia 'Pepride' is a new cultivar, distinguished by dark red dentate bracts, compact growth habit and self-branching characteristics. 'Pepride' is a sport of the red bracted '490' (U.S. Plant Pat. No. 7,825) with the same flowering response and cultural requirements. The new plant produces a very desirable branched flowering plant for smaller pots and hanging baskets. It is resistant to epinasty after being confined to shipping containers. The post-production foliage and bract retention are excellent.

1 Drawing Sheet

BACKGROUND OF THE NEW PLANT

Poinsettia plant 'Pepride' is the subject of an application for Plants Breeders' Rights protection in Denmark (PBR No. 16485); in the European Community (EC 95-0864); and in Germany (EUP 170).

This new poinsettia cultivar originated as a red bracted sport of '490' (U.S. Plant Pat. No. 7,825) in my greenhouse in Skibby, Denmark in 1994. It was induced through irradiation of vegetative plants with 2500 rads of γ radiation, and was selected from about 200 mutants so produced, because of its dark red bracts, strong self-branching, dark green leaves, compact growth habit and dentate leaves and bracts, traits which distinguish it from other poinsettia cultivars, and seemed to make it a desirable plant for commercial greenhouse production. Its compact size is ideal for smaller 2–12 cm pots and hanging baskets. 'Pepride' differed from its parent '490' in having dentate leaves and bracts compared to leaves and bracts with mostly entire margins. After selection, 'Pepride' was vegetatively reproduced from stem cuttings for test purposes in Encinitas, Calif. By subjecting clones of this plant to successive generations of vegetative propagation, it was demonstrated that the distinctive characteristics of 'Pepride' held true from generation to generation. Grown under the same greenhouse environment, 'Pepride' had a more compact growth habit but the same flowering response time as the parent plant '490'.

DESCRIPTION OF THE PHOTOGRAPHS

Poinsettia 'Pepride' is illustrated in the accompanying color photographs.

The upper photo is a side view of one branched plant per pot in full flower.

The lower photo is a top view of the same plant showing flower and bract formation.

DESCRIPTION OF THE PLANT

The following is a detailed description of this new poinsettia as observed in Encinitas, Calif., USA during December 1994. Observations were recorded from flowering plants, grown as one branched plant per pot. The pot was 14 cm in diameter and 11 cm in height. Color designations are compared to the 1986 edition of the R.H.S. Colour Chart, first published in 1966 by The Royal Horticultural Society, London, England.

THE PLANT

The following chart summarizes some of the differences between 'Pepride' and its parent poinsettia '490' (U.S. Plant Pat. No. 7,825).

| Plant | 'Pepride' | '490' |
|---|---|---|
| Plant height | 38 cm | 43 cm |
| Plant width | 40 cm | 48 cm |
| Leaf margin | Dentate | Mostly entire |

Origin: Sport of '490' (U.S. Plant Pat. No. 7,825), induced through irradiation of vegetative plants with 2400 rads of γ radiation.

Classification:

*Botanical.*—*Euphorbia pulcherrima* Willd.

*Common name.*—Poinsettia.

*Cultivar name.*—'Pepride'.

Form: Shrub.

Height: Short.

Growth habit: As a single stemmed plant, upright and vigorous with self-branching side shoots. The application of a chemical growth retardant may not be needed to restrict height for commercial pot plant production. I observed single branched plants in pots with an overall height of 38 cm and an overall width of 40 cm. The bract diameter of individual flowers was 25 cm.

Branching: Axillary branches will develop and terminate in a flower without pinching. However, it is usually desirable to pinch 'Peptide' before flower induction and remove all terminal dominance. Then, all axillary branches will develop uniformly and at a faster rate.

Growth rate: Rooting of stem cutting occurs in 12–18 days under intermittent mist.

Flowering: The plant will flower in eight weeks under continuous long night conditions and night temperatures of 16°–18° C. Like its parent, ('490'), 'Pepride' will be in full bloom in mid to late November in the northern hemisphere under natural daylength conditions.

Foliage: The foliage was clean and uniformly dark green from bottom to top of the plant. The leaves were of medium size, leaf blades typically being 10–11 cm long and 8 cm wide with leaf petioles 4 cm long.

*Leaf shape.*—Typical leaves are ovate with acute bases and acuminate tips. Leaf margins are strongly dentate, typically with two lobes on either side of the leaf blade.

*Leaf surface.*—The upper surface is glabrous and the under surface is slightly pubescent.

*Color.*—Upper side — Dark green, much darker than R.H.S. 147A. Under side — Green, near R.H.S. 147A.

*Retention.*—Foliage retention is excellent even under low light intensities in the consumer's home.

Bracts: Generally there were 10–12 red bracts of various sizes subtending the cyathia. The primary bracts had blades typically 13 cm long and 10–11 cm wide with petioles 2–3 cm long.

*Shape.*—Primary bracts are ovate with acute bases and acuminate tips. Bract margins are dentate with 2 lobes on either side of the bract. Secondary bracts are ovate to elliptic and have entire margins.

*Surface.*—The bract surface is slightly rugose.

*Color.*—Upper side — Dark bright red, near R.H.S. 46B. Under side — Red, R.H.S. 53 A-B.

Flowers: Generally, 8–10 cyathia (flowers) were present when the plant was in full bloom. Each cyathium is about 5 mm long and 5 mm wide, green in color, and fringed red at the distal end. One yellow nectar cup protrudes from the side of each cyathium. The flower pedicel is also green and about 5 mm in length. The stamens protruding from the cyathia are red. The stigmas are red and trifurcate. cyathia retention was about three weeks beyond the flower was fully mature.

*Nectar exudate.*—Present, abundant.

*Seed formation.*—Self-incompatible.

*Fertility.*—Not observed.

Post production: 'Pepride' was resistant to epinasty after being confined to shipping containers. The foliage and bract retention were excellent.

What is claimed is:

1. A new and distinct Poinsettia cultivar, substantially as herein shown and described, distinguished by its dark red dentate bracts, self branching, compact growth habit and excellent leaf and bract retention in the consumer environment.

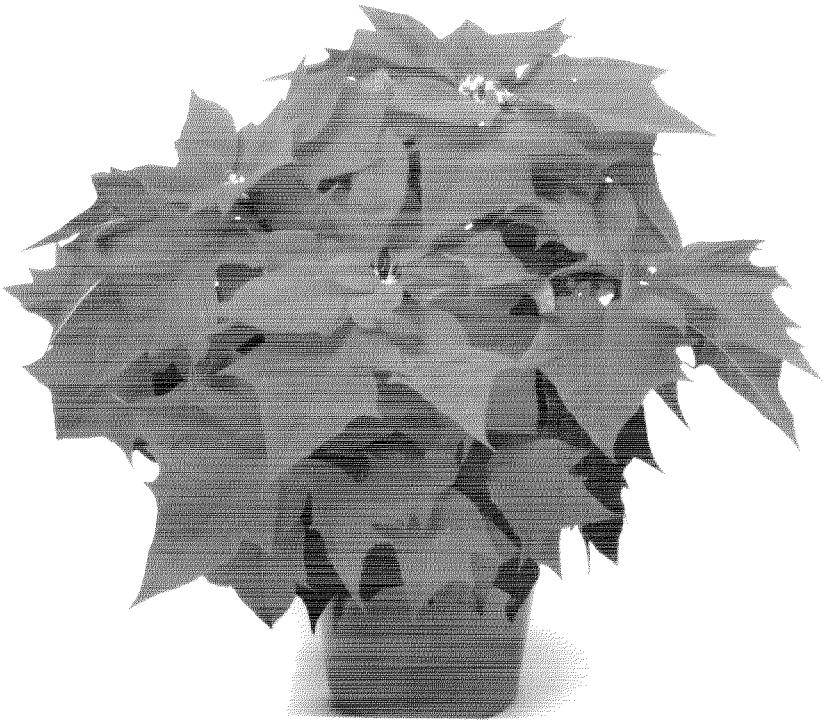
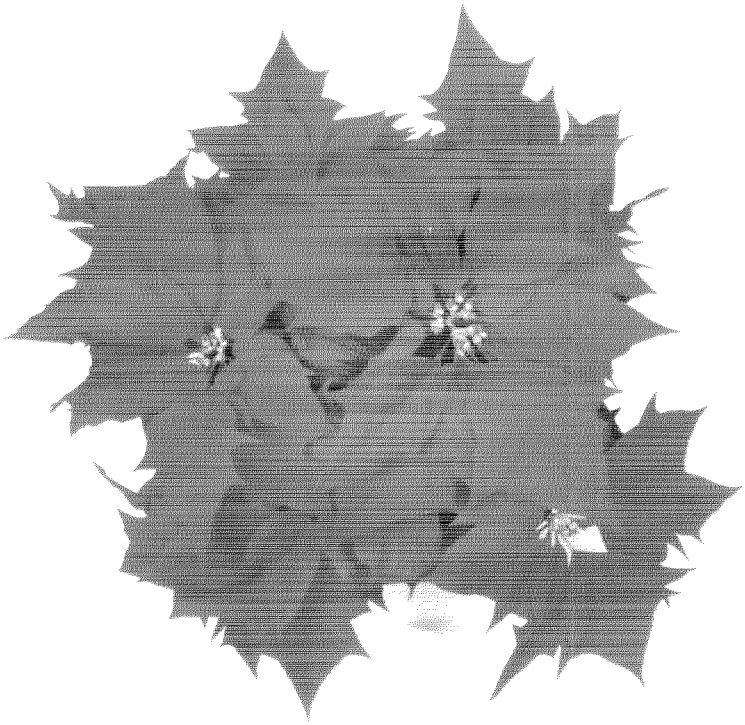

* * * * *